United States Patent [19]

Jautelat et al.

[11] 4,423,243
[45] Dec. 27, 1983

[54] PROCESS FOR THE PREPARATION OF 2,2-DIMETHYL-3-VINYL-CYCLO-PROPANECARBOXYLIC ACIDS AND ESTERS

[75] Inventors: Manfred Jautelat, Burscheid; Dieter Arlt, Cologne, both of Fed. Rep. of Germany

[73] Assignee: Bayer Aktiengesellschaft, Leverkusen, Fed. Rep. of Germany

[21] Appl. No.: 331,403

[22] Filed: Dec. 16, 1981

[30] Foreign Application Priority Data

Jan. 8, 1981 [DE] Fed. Rep. of Germany ....... 3100354

[51] Int. Cl.³ .......................................... C07C 69/743
[52] U.S. Cl. .............................. 560/124; 260/465 D; 548/479; 548/514; 549/79; 549/478; 549/498; 562/506; 560/101; 568/393; 568/419
[58] Field of Search ................ 560/124, 101; 562/506; 260/465 D; 549/79, 498, 478; 548/479, 514

[56] References Cited

FOREIGN PATENT DOCUMENTS 8340   3/1980 European Pat. Off. .
2621835 11/1976 Fed. Rep. of Germany .
2659973 9/1979 Fed. Rep. of Germany .

Primary Examiner—Michael L. Shippen
Attorney, Agent, or Firm—Sprung, Horn, Kramer & Woods

[57] ABSTRACT

A process for the production of 2,2-dimethyl-3-vinyl-cyclopropanecarboxylic acid derivative of the formula

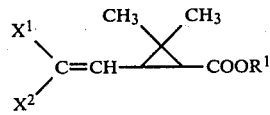

in which
R¹ is a hydrogen atom, an alkyl group or a radical of an alcohol which can be used in pyrethroids, and
X¹ and X² each independently is a halogen atom or a fluorine-substituted alkyl radical, comprising adding (a) a polyhalogenoalkene of the formula

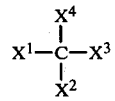

in which $X^3$ and $X^4$ each independently is a halogen atom, to 1-chloro-3,3-dimethyl-pent-4-en-2-one of the formula

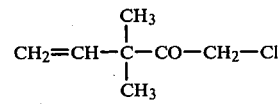

in the presence of a catalyst which yields free radicals, or in the presence of a metal salt of the VIII main group or of the sub-group IVa, VIIa or Ib of the periodic system, thereby to obtain a mixture of compounds of the formula

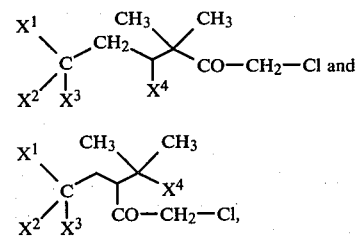

and (b) reacting either or both of such compounds with a base of a formula

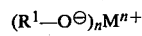

in which
M is an alkali metal or alkaline earth metal, and
n is 1 or 2.

The end products are known insecticides and intermediates therefor, while the intermediates produced by (a) are novel compounds.

7 Claims, No Drawings

PROCESS FOR THE PREPARATION OF 2,2-DIMETHYL-3-VINYL-CYCLOPROPANECARBOXYLIC ACIDS AND ESTERS

The present invention relates to an unobvious process for the preparation of certain known 2,2-dimethyl-3-vinyl-cyclopropanecarboxylic acids and esters thereof.

2,2-Dimethyl-3-vinyl-cyclopropanecarboxylic acid esters and certain processes for their preparation are known.

Amongst the numerous syntheses, the preparation processes via a rearrangement of α-halogenocyclobutanones (see DOS (German Published Specification) No. 2,638,356 and EP (European Patent) No. 2,207) are distinguished by good yields and the simple manner in which they are carried out. However, the preparation of the α-halogenocyclobutanones has to be effected via a multi-step synthesis. The yields obtainable in this process are not always completely satisfactory.

The present invention now provides a process for the production of a 2,2-dimethyl-3-vinyl-cyclopropanecarboxylic acid derivative of the general formula

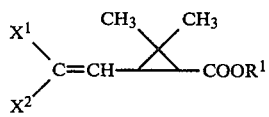

in which

R$^1$ represents a hydrogen atom, an alkyl group or a radical of an alcohol which can be used in pyrethroids, and X$^1$ and X$^2$ are identical or different and represent a halogen atom or a fluorine-substituted alkyl radical, characterized in that, (a) a polyhalogenoalkane of the general formula

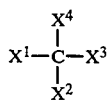

in which

X$^1$ and X$^2$ have the abovementioned meanings and

X$^3$ and X$^4$ are identical or different and represent a halogen atom, is added to 1-chloro-3,3-dimethyl-pent-4-en-2-one of the formula

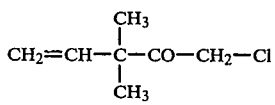

in the presence of a catalyst which yields free radicals, or in the presence of a metal salt of the VIII main group or of the sub-group IVa, VIIa or Ib of the periodic system, and (b) the compounds which are obtained thereby of the formulae

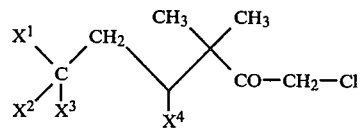

and

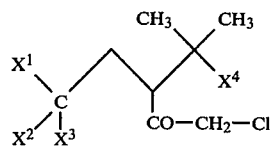

in which X$^1$, X$^2$, X$^3$ and X$^4$ have the abovementioned meanings, are reacted individually or in a mixture, with a base of the general formula

in which

R$^1$ has the abovementioned meanings,

M represents an alkali metal or alkaline earth metal, and n is 1 or 2.

The present invention also provides, as new compounds, the compounds of formulae (IV) and (V), as defined above, especially 1,4,6,6,6-pentachloro-3,3-dimethyl-hexan-2-one and 1,4-dichloro-4-methyl-3-(2,2,2-trichloroethyl)-pentan-2-one, respectively.

It is decidedly surprising that the radical addition of a polyhalogenoalkane of the formula (II) to the unsaturated ketone of the formula (III) leads, with rearrangement, to isomeric products of the formula (V), in addition to the direct addition products of the formula (IV). According to the state of the art (see Houben-Weyl, Methoden der Org. Chemie (Methods of Organic Chemistry), V/3, page 971), a rearrangement under these conditions was not to be expected. Still more surprising, however, is the fact that each of these isomeric adducts (IV) and (V) as well as a mixture thereof yields a cis/trans mixture of the 2,2-dimethyl-3-vinyl-cyclopropanecarboxylic acid derivative of the formula (I) on treatment with an alcoholate or hydroxide.

The process according to the invention has a number of advantages. Thus, with the action of a base on the compounds of formulae (IV) and (V), the vinylcyclopropanecarboxylic acid derivative of the formula (I) is obtained directly in good yields and purity, without having to isolate any intermediate stages occurring in the process.

Furthermore, the compounds of formulae (IV) and (V) do not need to be separated, but can be used as a mixture. The starting material of the formula (III), namely 1-chloro-3,3-dimethyl-pent-4-en-2-one, can also be prepared in a simple manner from reasonably priced, industrially readily available substances, namely isoprene and vinylidene chloride.

If, for example, tetrachloromethane is used as the starting material, the course of the reaction according to the present invention is illustrated by the following equation:

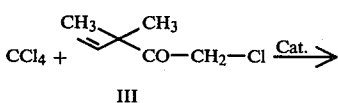

III

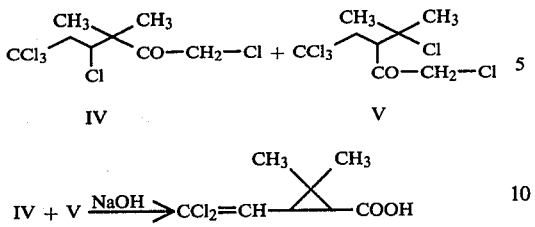

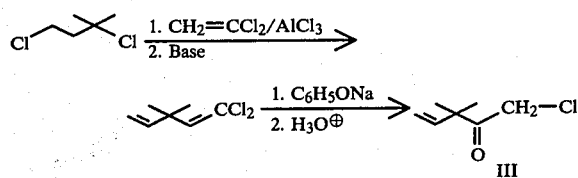

Preferred polyhalogenoalkanes of formula (II) used as starting materials are those in which $X^1$ and $X^2$, which can be identical or different, represent a chlorine, bromine or fluorine atom or a perfluorinated alkyl radical having 1 to 3 carbon atoms, and $X^3$ and $X^4$, which likewise can be identical or different, represent a chlorine or bromine atom.

The following compounds may be individually mentioned as examples of the polyhalogenoalkanes which can be used according to the invention: tetrachloromethane, tetrabromomethane, chlorotribromomethane, dichlorodifluoromethane, bromochlorodifluoromethane, iodotrichloromethane, 1,1,1-trichloro-trifluoroethane, 1,1,1-tribromotrifluoroethane, 1,1-dibromo-tetrafluoroethane, 2,2-dibromo-1,1,1,3,3,3-hexafluoropropane, 1,1,1,3-tetrachlorotetrafluoropropane and 1,1,1-trichloropentafluoropropane.

The compound of the formula (III) can be prepared in a simple manner according to the following process.

The addition of hydrogen chloride to isoprene leads to dichloroisopentane, which adds to vinylidene chloride and undergoes an elimination reaction with bases to give 1,1-dichloro-3,3-dimethyl-1,4-pentadiene. Reaction with sodium phenolate and hydrolysis yields the chloromethyl ketone of the formula (III):

The addition according to process step (a) is carried out at normal pressure, but in the case of low-boiling compounds of the formula (II) it is preferably carried out under pressure.

The pressure range can vary within wide limits, about between 1 and 30 bars, preferably between 3 and 15 bars. The increased pressure can be achieved by pressurizing an inert gas (such as nitrogen).

The reaction temperature can be a temperature between 50° and 200° C., but the reaction is preferably carried out between 80° and 150° C. A diluent is added, if appropriate, to the two starting materials of the formulae (II) and (III).

Aliphatic or aromatic hydrocarbons (such as benzene or toluene), alcohols (such as methanol, ethanol, propanol or tert.-butanol), nitriles (such as acetonitrile or propionitrile) and dimethylformamide are suitable diluents. Alcohols, acetonitrile and dimethylformamide are preferred.

Catalysts are required for carrying out the reaction, namely, either (a) catalysts which yield free radicals, such as azobisisobutyronitrile, benzoyl peroxide of di-tert.-butyl peroxide, or (b) metal salts of the VIII main group and the subgroup IV a, VII a and I b of the periodic system, examples which may be mentioned being: copper (II) oxide, iron (III) oxide; Cu(I), Cu(II), Fe(II) and Fe(III) bromides and, especially, chlorides, and the chlorides of ruthenium, rhodium, palladium, cobalt and nickel Cu(II) sulphate, Fe(II) and Fe(III) sulphate; Cu(II) nitrate and iron (III) nitrate; manganese(III) acetate, copper (II) acetate; copper (II) stearate; iron(III) citrate; Cu(I) cyanide; ruthenium (II) dichloro-tris-triphenylphosphine, rhodium-tris(triphenylphosphine) chloride; chromium and nickel acetylacetonate, copper (II) acetylacetonate, iron(III) acetylacetonate, cobalt-(II) and cobalt(III) acetylacetonate, manganese(II) acetylacetonate, copper(II) benzoylacetonate; iron carbonyl-cyclopentadienyl complex; molybdenum carbonyl-cyclopentadienyl complex, ruthenium(II) acetate complex, chromium and molybdenum hexacarbonyl, nickel tetracarbonyl, iron pentacarbonyl, and cobalt and manganese carbonyl, or (c) catalyst mixtures which consist of one of the above metal salts, an amine and, if appropriate, some benzoin. The metal salt can also be present as the hydrate, and the amine can also be present as the salt, for example as the hydrochloride. Examples of amines are: dimethylamine, diethylamine, trimethylamine, triethylamine, diisopropylamine, n-butylamine, benzylamine, ethanolamine, aniline and pyridine. Dimethylamine, diethylamine (as the hydrochlorides), and n- butylamine are preferred.

At least about 1.5 mols, preferably about 2 to 10 mols, of organic amine per mol of metal salt are employed. The metal salt is employed in quantities of about 0.01 to 15 mol%, preferably about 0.05 to 10 mol%, relative to compounds of the formula (II).

The addition of equimolar quantities of benzoin, relative to the metal salt, is often advantageous.

The reaction components of the formulae (II) and (III) are employed in equimolar quantities. The polyhalogenoalkane (II) is preferably used in excess or even as a diluent.

The addition products obtained, which are of the formula (IV) and (V), are reacted as a mixture or, after a separation process, individually with bases of the formula (VI) (process step b)).

In formula (VI), $R^1$ preferably represents a hydrogen atom, an alkyl radical having 1 to 6 carbon atoms or the radical of an alcohol which can be used in insecticidal pyrethroids and M preferably represents an alkali metal, particularly sodium and potassium.

The following compounds may be individually mentioned as examples of bases: sodium hydroxide, potassium hydroxide, sodium methylate, sodium ethylate, sodium butylate and potassium tert.-butylate, and the alkali metal salts of the following alcohols: 5-benzyl-3-hydroxymethyl-furan, 5-benzyl-2-hydroxymethyl-furan, 5-benzyl-3-hydroxymethyl-thiophene, 5-phenoxy-5-hydroxymethyl-furan, 3-hydroxy-4-methyl-5-allyl-cyclopent-4-en-1-one, N-hydroxymethyl-phthalimide, N-hydroxymethyl-3,4,5,6-tetrahydrophthalimide, pentafluorobenzyl alcohol, 4-phenyl-3-chloro-2-buten-1ol, 3-trifluoromethoxybenzyl alcohol, 3-dichlorovinyloxybenzyl alcohol, 3-propargyloxybenzyl alcohol, 3-dichlorovinyloxy-α-cyano-benzyl alcohol, 3-phenoxybenzyl alcohol, 3-phenyloxy-α-cyanobenzyl alcohol, 3-phenoxy-α-methoxycarbonyl-benzyl alcohol, 3-phenoxy-α-ethinyl-benzyl alcohol, 3-phenoxy-4-fluoro-benzyl alcohol, 3-(4'-fluorophenoxy)-benzyl alcohol, 3-(4'-chlorophenoxy)-benzyl alcohol and 3-(4'-bromophenoxy)-benzyl alcohol.

Principally, water and alcohols (such as methanol, ethanol, n-propanol, iso-propanol, butanol, tert.-butanol, glycol, glycol monomethyl ether or the alcohols belonging to the alcoholates employed) are suitable diluents in the process step (b). Furthermore, hydrocarbons (such as benzene and toluene), chlorinated hydrocarbons (such as methylene chloride and chlorobenzene), ethers (such as tetrahydrofuran, dioxane and dimethoxyethane), or polar solvents (such as dimethylformamide, dimethylsulphoxide and hexamethylphosphoric acid triamide) are suitable. Two-phase systems (such as toluene/water or methylene chloride/water) in combination with customary ammonium salts, phosphonium salts or crown ethers as phase transfer catalysts are also suitable.

The reaction temperatures can be varied within a relatively wide range. In general, the reaction is carried out at a temperature between 20° and 180° C., preferably between 50° and 120° C.

The reaction is carried out at normal pressure, but can also be carried out under pressure.

In carrying out the process according to the invention (process step (b)), about 3 to 6 equivalents of bases of the formula (VI) are employed per mol of adduct of the formulae (IV) or (V). A greater excess of base is also possible.

The examples which follow illustrate the process according to the invention.

Preparation of 1-chloro-3,3-dimethyl-pent-4-en-2-one (a compound of formula (III))

EXAMPLE 1

(a) 1-Chloro-3,3-dimethyl-2-phenoxy-1,4-pentadiene 116 g (1 mol) of sodium phenolate and 82.5 g (0.5 mol) of 1,1-dichloro-3,3-dimethyl-1,4-pentadiene were heated under reflux in 500 ml of dimethylformamide for 18 hours. The solution was diluted with methylene chloride and was extracted by shaking with dilute sodium hydroxide solution. After the $CH_2Cl_2$ phase had been dried over $Na_2SO_4$, the solvent was stripped off in vacuo. 108.5 g (0.488 mol, 97%) of crude product remained, and this product was distilled. 93.6 g (0.42 mol, 84%) of 1-chloro-3,3-dimethyl-2-phenoxy-1,4-pentadiene passed over at a boiling point of 80° to 90° C./0.5 mm Hg.

NMR ($CDCl_3$): $\delta 1.25$ (s, 6H), 4.9–6.2 ($-CH=CH_2$), 5.85 (s, 1H), 6.8–7.4 (m, 5H).

(b) 1-Chloro-3,3-dimethyl-pent-4-en-2-one 57 g (0.256 mol) of 1-chloro-3,3-dimethyl-2-phenoxy-1,4-pentadiene were warmed to 40° C. in a mixture of 250 ml of formic acid and 50 ml of concentrated hydrochloric acid for 1 hour. The mixture was then diluted with 400 ml of $CH_2Cl_2$ and ice, and was extracted 3 times by shaking with 2 N sodium hydroxide solution. After the methylene chloride phase had been dried over $Na_2SO_4$, the solvent was stripped off in a rotary evaporator. There remained 36 g (96%) of crude product. 32.2 g (0.22 mol, 86%) of 1-chloro-3,3-dimethyl-pent-4-en-2-one were obtained by distillation (b.p. 81°–84° C./24 mm Hg).

NMR ($CDCl_3$): $\delta 1.3$ (s, 6H), 4.35 (s, 2H), 5.0–6.2 ($-CH=CH_2$).

Addition of carbon tetrachloride to a compound of formula(III)

EXAMPLE 2

14.65 g (0.1 mol) of 1-chloro-3,3-dimethyl-pent-4-en-2-one (a compound of formula (III)) were heated under reflux under nitrogen in 50 ml of tetrachloromethane in the presence of 0.9 g (0.001 mol) of tris-(triphenylphosphine)-ruthenium dichloride for 25 hours. After the mixture had been filtered and the solvent had been stripped off in vacuo, the mixture was distilled under a vacuum from an oil pump. 24.0 g (80 mmols, 80%) of an adduct mixture composed of 40% of 1,4,6,6,6-pentachloro-3,3-dimethylhexan-2-one (a compound of formula (IV) and 60% of 1,4-dichloro-4-methyl-3-(2,2,2-trichloroethyl)-pentan-2-one (a compound of formula (V)) were isolated at a boiling point of 130°–140°/0.5 mm Hg.

The compound of formula IV:
NMR ($CDCl_3$): $\delta 1.3$ (s, 3H), 1.35 (s, 3H), 3.1 (m, 2H) 4.4–4.5 (m, 3H)

The compound of formula V:
NMR ($CDCl_3$): $\delta 1.6$ (s, 3H), 1.65 (s, 3H), 2.8–3.8 (m, 3H) 4.45 (AB, 2H).

EXAMPLE 3

14.65 g (0.1 mol) of 1-chloro-3,3-dimethyl-pent-4-en-2-one (a compound of formula (III)) were heated to 120° C. under nitrogen with 47 g (0.3 mol) of tetrachloromethane in 50 ml of dimethylformamide in the presence of 1.3 g of $FeCl_3.6H_2O$, 1.1 g of benzoin and 0.4 g of dimethylamine hydrochloride for 12 hours. The mixture was diluted with methylene chloride and was extracted several times by shaking with water. The distillation yielded 25.6 g (85 mmols, 85%) of an adduct mixture at a boiling point of 133° to 145° C./0.6 mm Hg, the adduct mixture containing approximately 90% of a compound of formula (V) and 10% of a compound of formula (IV).

Preparation of 2,2-dimethyl-3-(2,2-dichlorovinyl)-cyclopropane-carboxylic acid and ester

EXAMPLE 4

6.0 g (20 mmols) of the adduct mixture of the compounds of formulae (IV) and (V)(prepared as described in Example 3) were heated under reflux for 6 hours with 4 g (0.1 mol) of sodium hydroxide in 40 ml of water. The clear aqueous solution was purified by shaking with methylene chloride, the latter being discarded. The solution was then acidified with hydrochloric acid and was extracted with $CH_2Cl_2$. 4.1 g (19.6 mmols) of 2,2-dimethyl-3-(2,2-dichlorovinyl)-cyclopropanecarboxylic acid (permethrinic acid) were obtained as a cis/trans mixture (gas chromatography: 43% cis acid and 38.3% trans acid) from the methylene chloride solution after the latter had been dried and the solvent stripped off.

NMR ($CDCl_3$): $\delta 1.2–1.4$ (m, 6H), 1.5–2.4 (m, 2H), 5.65 and 6.25 (2 d, 1H), 10.6 (s, 1H).

EXAMPLE 5

3 0 g (0.1 mol) of the adduct mixture of the compounds of the formulae (IV) and (V) (prepared as described in Example 3) were heated under reflux for 5 hours with 22.5 g (0.4 mol) of KOH in 300 ml of water. The working-up according to Example 4 yielded 17.7 g (85 mmols, 85%) of 2,2-dimethyl-3-(2,2-dichlorovinyl)-cyclopropanecarboxylic acid (permethrinic acid): 50.2% cis and 41.0% trans acid.

EXAMPLE 6

3.9 g (13 mmols) of the adduct mixture of the compounds of formulae (IV) and (V) (prepared as described in Example 3) were heated under reflux for 5 hours with 2.6 g (65 mmols) of NaOH in 30 ml of ethanol. The working up with methylene chloride and dilute hydrochloric acid led to 2.35 g (11.3 mmols), 87%) of permethrinic acid as a cis/trans mixture.

EXAMPLE 7

6 g (20 mmols) of the adduct mixture of the compounds of formulae (IV) and (V) (prepared as described in Example 3) were added to the solution of 2.3 g (0.1 mol) of sodium in 100 ml of absolute ethanol, and the mixture was heated under reflux for 8 hours. The mixture was acidified and was extracted by shaking with $CH_2Cl_2$. The distillation yielded 3.7 g (15.6 mmols, 78%) of cis and trans permethrinic acid ethyl ester at a boiling point of 94° to 98° C.)/0.15 mm Hg.

2,2-Dimethyl-3-(2-chloro-3,3,3-trifluoro-1-propenyl)-cyclopropanecarboxylic acid

EXAMPLE 8

14.56 g (0.1 mol) of 1-chloro-3,3-dimethyl-pent-4-en-2-one of formula (III) were heated under nitrogen to 120° C. with 10.45 g (0.05 mol) of 1,1,1-trichlorotrifluoroethane in 50 ml of dimethylformamide in the presence of 1.3 g of $FeCl_3.6H_2O$, 1.1 g of benzoin and 0.4 g of dimethylamine hydrochloride for 10 hours. The mixture was then worked up using methylene chloride and water. Ater the dried solvent had been stripped off, 22 g of crude product remained, and this product was fractionally distilled. The adduct mixture (boiling point 130°-150°/20 mm Hg) contained 3-(2-chloro-2-propyl)-1,5,5-trichloro-6,6,6-trifluoro-hexan-2-one as the principal product.

NMR ($CDCl_3$): δ1.65 (s, 6H), 2.4-3.9 (m, 3H), 4.6 (s, 2H)

EXAMPLE 9

7.1 g (20 mmols) of the adduct from Example 8 were heated under reflux for 6 hours with 4 g (0.1 mol) of NaOH in 40 ml of water. The working-up according to Example 4 led to 4.7 g (19.4 mmols, 97%) of 2,2-dimethyl-3-(2-chloro-3,3,3-trifluoro-1-propenyl)-cyclopropanecarbocxylic acid as an isomer mixture of melting point 67°-77°.

2,2-Dimethyl-3-(2,2-dibromovinyl)-cyclopropanecarboxylic acid

EXAMPLE 10

14.65 g (0.1 mol) of 1-chloro-3,3-dimethyl-pent-4-en-2-one of formula (III) and 33.2 (0.1 mol) of tetrabromomethane were heated to 90° C. for 35 hours, approximately 1 g of dibenzoyl peroxide being successively added to the mixture. The working-up with $CH_2Cl_2$ and water led to 47 g of crude product, and this product was fractionally distilled. The adduct mixture composed of 1-chloro-4-bromo-4-methyl-3-(2,2,2-tribromomethyl)-pentan-2-one and 1-chloro-3,3-dimethyl-4,6,6,6-tetrabromo-hexan-2-one was separated out at a boiling point of 160°-200°/0.09 mm Hg.

EXAMPLE 11

9.56 g (20 mmols) of the adduct mixture from Example 10 were stirred with 4 g (0.1 mol) of NaOH in 80 ml of water for 4 hours at room temperature and for 1 hour at 80° C. The working-up according to Example 4 yielded 4.94 g (16.6 mmols, 83%) of 2,2-dimethyl-3-(2,2-dibromovinyl)-cyclopropanecarboxylic acid as an isomer mixture in which the cis compound predominated.

NMR ($CDCl_3$): δ1.25-1.35 (4s, 6H), 1.6-2.2 (m, 2H), 6.2 and 6.75 (d, 1H).

It will be appreciated that the instant specification and examples are set forth by way of illustration and not limitation, and that various modifications and changes may be made without departing from the spirit and scope of the present invention.

We claim:

1. A process for the production of 2,2-dimethyl-3-vinyl-cyclopropanecarboxylic acid derivative of the formula

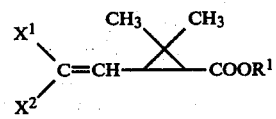

in which $R^1$ is a hydrogen atom, an alkyl group or a radical of an alcohol selected from the group consisting of 5-benzyl-3-hydroxymethyl-furan, 5-benzyl-2-hydroxymethyl-furan, 5-benzyl-3-hydroxymethyl-thiophene, 5-phenoxy-5-hydroxymethyl-furan, 3-hydroxy-4-methyl-5-allyl-cyclopent-4-en-1-one, N-hydroxymethyl-phthalimide, N-hydroxymethyl-3,4,5,6-tetrahydrophthalimide, pentafluorobenzyl alcohol, 4-phenyl-3-chloro-2-buten-1ol, 3-trifluoromethoxybenzyl alcohol, 3-dichlorovinyloxybenzyl alcohol, 3-propargyloxybenzyl alcohol, 3-dichlorovinyloxy-α-cyano-benzyl alcohol, 3-phenoxybenzyl alcohol, 3-phenyloxy-α-cyano-benzyl alcohol, 3-phenoxy-α-methoxycarbonyl-benzyl alcohol, 3-phenoxy-α-ethinyl-benzyl alcohol, 3-phenoxy-4-fluoro-benzyl alcohol, 3-(4'-fluorophenoxy)-benzyl alcohol, 3-(4'-chlorophenoxy)-benzyl alcohol and 3-(4'-bromophenoxy)-benzyl alcohol, and $X^1$ and $X^2$ each independently is a halogen atom or a fluorine-substituted alkyl radical, comprising adding (a) a polyhalogeno alkane of the formula

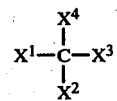

in which $X^3$ and $X^4$ each independently is a halogen atom, to 1-chloro-3,3-dimethyl-pent-4-en-2-one of the formula

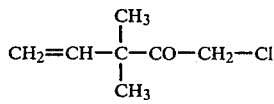

in the presence of a catalyst which yields free radicals, or in the presence of a metal salt of the VIII main group or of the sub-group IVa, VIIa or Ib of the periodic system, thereby to obtain a mixture of compounds of the formula

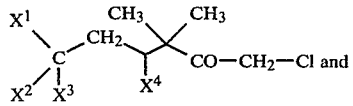

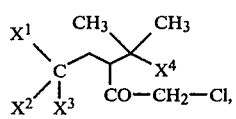

(b) reacting either or both of such compounds with a base of the formula

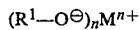

in which
M is an alkali metal or alkaline earth metal, and
n is 1 or 2.

2. A process according to claim 1, wherein step (a) is carried out at a temperature between about 50° and 200° C.

3. A process according to claim 1, wherein step (a) is carried out in an alcohol, acetonitrile or dimethylformamide as solvent.

4. A process according to claim 1, in which
$X^1$ and $X^2$ each independently is chlorine, bromine, fluorine or a perfluorinated alkyl radical having 1 to 3 carbon atoms, and
$X^3$ and $X^4$ each independently is chlorine or bromine.

5. A process according to claim 1, wherein step (b) is carried out at a temperature between about 20° and 180° C.

6. A process according to claim 1, wherein step (b) is carried out in water or an alcohol as a diluent or in a two-phase system in combination with an ammonium salt, phosphonium salt or crown ether as phase transfer catalyst.

7. A process according to claim 4, wherein step (a) is carried out at a temperature between about 50° and 200° C. in an alcohol, acetonitrile or dimethylformamide as solvent, and step (b) is carried out at a temperature between about 20° and 180° C. in water or an alcohol as a diluent or in a two-phase system in combination with an ammonium salt, phosphonium salt or crown ether as phase transfer catalyst.

* * * * *